United States Patent [19]

Redmore et al.

[11] 4,085,134
[45] Apr. 18, 1978

[54] AMINO-PHOSPHONIC-SULFONIC ACIDS

[75] Inventors: Derek Redmore, Ballwin; Frederick T. Welge, Affton, both of Mo.

[73] Assignee: Petrolite Corporation, St. Louis, Mo.

[21] Appl. No.: 442,778

[22] Filed: Feb. 15, 1974

[51] Int. Cl.² .............................................. C07F 9/38
[52] U.S. Cl. ............................. 260/502.5; 21/2.7 A; 210/58; 252/180
[58] Field of Search ..................................... 260/502.5

[56] References Cited

U.S. PATENT DOCUMENTS

| | | | |
|---|---|---|---|
| 2,673,213 | 3/1954 | Bersworth | 260/502.5 |
| 2,961,311 | 11/1960 | Bersworth et al. | 260/502.5 |
| 3,703,545 | 11/1972 | McCrary | 260/513 N |

Primary Examiner—Joseph E. Evans
Attorney, Agent, or Firm—Sidney B. Ring; Hyman F. Glass

[57] ABSTRACT

This invention relates to compounds characterized by the presence of N-methyl, or substituted methyl, phosphonic acid and N-propylenesulfonic acid groups. These compounds contain at least one or more of each group and are bonded to the same or different amino groups. They are derived by reacting an amine with both propane sultone and with a carbonyl compound, such as formaldehyde, and phosphorous acid or its equivalent.

They have a wide variety of uses, for example as scale and corrosion inhibitors, chelating agents, etc.

10 Claims, No Drawings

AMINO-PHOSPHONIC-SULFONIC ACIDS

The compounds of this invention may be presented by the following idealized formula $$N \begin{cases} [(CH_2)_3SO_3H]_n \\ \left[ CH_2\overset{O}{\underset{\|}{P}}(OH)_2 \right]_m \end{cases}$$

where N is an amino moiety and $n$ and $m$ are at least 1, such as 1–5, for example from 1–3, but preferably 1.

In the case of a monoamine, $n$ and $m$ are 1. In the case of polyamine $n$ and $m$ can vary widely depending on the number of amino groups. Theoretically, the sum of $n + m$ can be equal to the number of replaced amino hydrogens. In general, the sulfonic acid groups are 1–2 or more and the phosphonic acid groups are 1–5 or more.

Any amine capable of reacting with propane sultone can be employed for example any amine having at least one primary amino group. Where the amine has more than one primary amino group, the number of sulfonic acid groups in the product will depend on the moles of sultone employed, for example $$NH_2-Z-NH_2 \xrightarrow{1M}$$

$$NH_2-Z-\underset{H}{N}-(CH_2)_3SO_3H \longrightarrow$$

$$HO_3S(CH_2)_3\underset{H}{N}-Z-\underset{H}{N}-(CH_2)_3SO_3H$$

Theoretically, some or all of the remaining nitrogen-bonded hydrogens can be converted to the methyl phosphonic acid depending on the stoichiometry of the reactants.

Any amino group having a reactive N-hydrogen group which is capable of reacting with a carbonyl compound and phosphorous acid or equivalent can be reacted to yield the compounds of this invention.

The aminomethyl phosphonic acids of this invention and their salts may be prepared by various methods. One method comprises reacting (1) an amine having reactive hydrogens attached to a nitrogen atom (2) a carbonyl compound such as an aldehyde or a ketone and (3) phosphorous acid, usually in the form of the dialkyl phosphite. The free N-aminomethyl phosphonic acids and their salts may be prepared by hydrolysis of the phosphonic ester under acid conditions such as with strong mineral acid such as HCl and the like.

These may be illustrated by the following reaction:

$$-NH + \underset{Y}{\overset{X}{\underset{|}{C}}}=O + (RO)_2\overset{O}{\underset{\|}{P}}-H \longrightarrow$$

$$N-\underset{Y}{\overset{X}{\underset{|}{C}}}-\overset{O}{\underset{\|}{P}}-(OR)_2 + H_2O$$

In the above equation X and Y are hydrogen or a substituted group such as an alkyl or aryl group, etc.

Phosphonic esters are converted to phosphonic acids or salts thereof according to the following reaction $$-N-\underset{Y}{\overset{X}{\underset{|}{C}}}-\overset{O}{\underset{\|}{P}}-(OR)_2 \xrightarrow{HCl} N-\underset{Y}{\overset{X}{\underset{|}{C}}}-\overset{O}{\underset{\|}{P}}(OH)_2$$

and other corresponding reactions.

Salts of these can also be prepared, for example salts containing metal, ammonium, amine, etc. groups such as sodium, potassium, triethanolamine, diethanolamine.

A second method comprises reacting (1) an amine (2) a carbonyl compound such as aldehyde or a ketone and (3) phosphorous acid preferably in presence of a strong mineral acid such as hydrochloric acid. This method yields the aminomethyl phosphonic acids directly.

This may be illustrated by the following reaction:

$$-NH + \underset{Y}{\overset{X}{\underset{|}{C}}}=O + HP(OH)_2 \longrightarrow -N-\underset{Y}{\overset{X}{\underset{|}{C}}}-\overset{O}{\underset{\|}{P}}(OH)_2$$

The general synthetic procedure involves two steps:
(a) Reaction of a primary amine with propane sultone to form a γ-amino sulfonic acid and (b) reaction of this molecule with formaldehyde and phosphorous acid.

$$RNH_2 + \begin{array}{c} CH_2 \\ | \\ CH_2 \\ | \\ CH_2 \end{array}\begin{array}{c} \\ \diagdown \\ O \\ \diagup \\ SO_2 \end{array} \longrightarrow R-NH-(CH_2)_3SO_3H \quad (a)$$

$$RNH(CH_2)_3SO_3H + HCHO + H_3PO_3 \longrightarrow \quad (b)$$

$$R-N\begin{array}{c}(CH_2)_3SO_3H \\ \diagdown \\ \diagup \\ CH_2\overset{O}{\underset{\|}{P}}(OH)_2\end{array}$$

This reaction is applicable to a wide range of amines; thus R can be alkyl such as $CH_3$, $C_2H_5$, $C_3H_7$, $C_4H_9$, $C_6H_{13}$, $C_8H_{17}$, $C_{12}H_{25}$, $C_{18}H_{37}$, etc., straight chained or branched such as isopropyl, 2-ethyl hexyl, etc., cyclic aliphatic groups such as cyclopentyl, cyclohexyl.

Other amines which can be reacted include polyamines such as polyalkylene polyamines for example of the formula $$NH_2\left(\underset{AN}{\overset{H}{|}}\right)_n H$$

where A is alkylene for example having 2–10 carbons or more and $n = 1$ to 10 or more, for example diamines such as ethylene diamine, propylene diamine, diethylene triamine, N-substituted 1,3,-propylene diamines, etc.

Amines suitable for this process include the following:
n-Butyl amine
2-ethyl hexyl amine
Monoisopropanolamine
Hexylamine
Heptylamine
Octylamine
Decylamine
Furfurylamine Dodecylamine
Monoethanolamine
n-Amylamine
Sec-amylamine
2-amino-4-methylpentane
4-amino-2-butanol
5-isopropylamino-1-pentanol Also, high molecular weight aliphatic amines known as Armeen 10, Armeen 16D, Armeen HTD, Armeen 18D, and Armeen CD can be used ($RNH_2$).

Other amines include:
2-amino-2-methyl propanol
2-amino-2-methyl-1,3-propanediol
2-amino-2-ethyl-1,3-propanediol
3-amino-2-methyl-1-propanol
2-amino-1-butanol
3-amino-2,2-dimethyl-1-propanol
2-amino-2,3-dimethyl-1-propanol
2,2-diethyl-2-amino ethanol
2,2-dimethyl-2-amino ethanol
3-amino-1,2-butanediol
4-amino-1,2-butanediol
2-amino-1,3-butanediol
4-amino-1,3-butanediol
2-amino-1,4-butanediol
3-amino-1,4-butanediol
1-amino-2,3-butanediol Amines having ring structures include cyclohexylamine, and various comparable amines with alkyl substituents in the ring.

A wide variety of polyamines also can be employed. These include the polyalkylene polyamines such as of the formula:

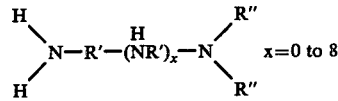

in which R" is hydrogen, alkyl, cycloalkyl, aryl, or aralkyl and R' is a divalent radical such as:

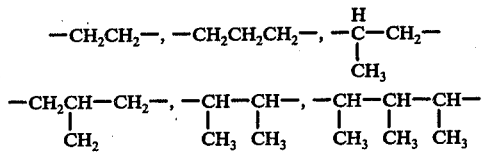

Examples of suitable polyamines include:
Ethylenediamine
Diethylenetriamine
Triethylenetetramine
Tetraethylenepentamine
Propylenediamine
Dipropylenetriamine
Tripropylenetetramine
Butylenediamine
Aminoethylpropylenediamine
Aminoethylbutylenediamine

Other polyamines in which the nitrogen atoms are separated by a carbon atom chain having 4 or more carbon atoms include the following: Tetramethylenediamine, pentamethylenediamine, hexamethylenediamine, etc.

If desired, one can prepare a variety of reactants having two or more amino groups and at least one hydroxyl group. One may use modifications of procedures or the procedures themselves as described in U.S. Pat. Nos. 2,046,720, dated July 7, 1936, to Bottoms; 2,048,990 dated July 28, 1936, to Britton et al.; 2,447,821 dated Aug. 24, 1949, to Sankus; and 1,985,885 dated Jan. 1, 1935, to Bottoms. Examples include the following:

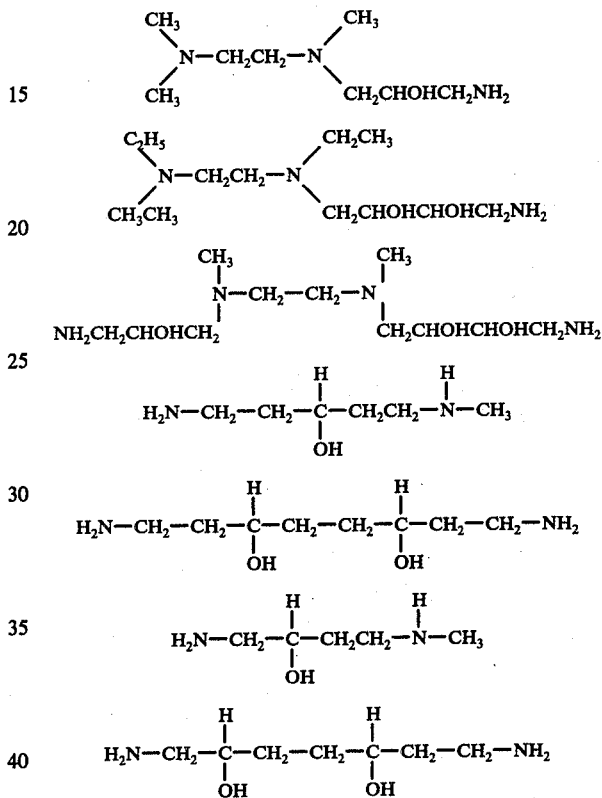

Other suitable amines are exemplified by ethylenebisoxypropylamine,

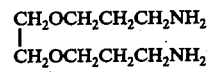

Another example of polyamines which may be employed as a reactant is the kind described as "Duomeens."

Duomeen is a trademark designation for certain diamines. Duomeen has the following general formula:

R is an alkyl group derived from a fatty acid or from the mixed fatty acids as obtained from certain oils. The specific Duomeen and the source of the radical R are as follows:
Duomeen 12, R = lauric
Duomeen C, R = Coconut oil fatty acid Similarly, a comparable diamine, presumably obtained from Rosin Amine D and acrylonitrile, can be prepared. The structure of Rosin Amine D is as follows:

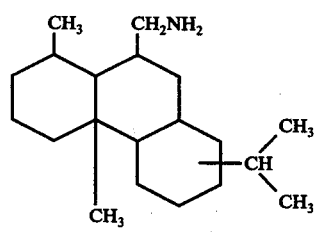

Polyamines from monoamines and cyclic imines, such as ethylene imine.

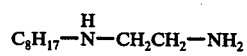

N-octyl ethylenediamine

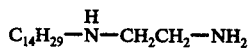

N-tetradecyl ethylenediamine

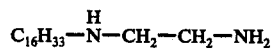

N-hexadecylethylenediamine

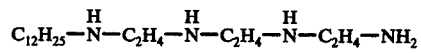

N-dodecyl triethylenetetramine

N-dodecyl propylenediamine

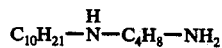

N-decyl butylenediamine

It is to be noted that all the above examples show high molal groups, i.e., 8 carbon atoms or more. The same derivatives in which methyl, ethyl, propyl, butyl, amyl, hexyl groups, or the like, appear instead of octyl, decyl, etc., are equally satisfactory.

Cyclic amidines, such as imidazolines and tetrahydropyrimidines, having an amino side chain can be reacted, for example:

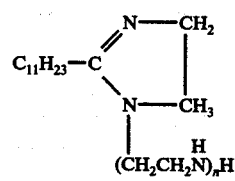

1-polyethyleneamine, 2-undecylimidazoline

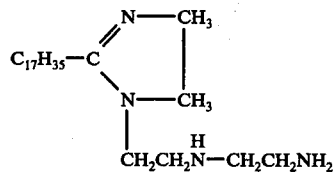

1-diethylene diamine, 2-heptadecylimidazoline

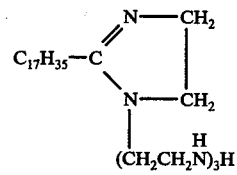

1-triethylenetriamine, 2-oleylimidazoline

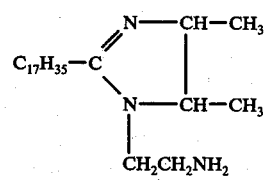

1-amino ethyl, 2-heptadecyl-4,5,dimethylimidazoline

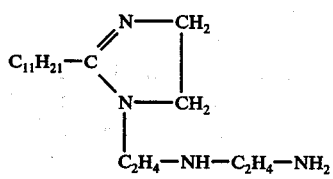

1-diethylenediamine, 2-undecylenecylimidazoline

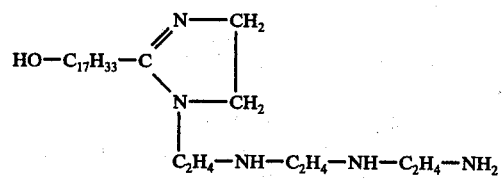

1-triethylenetriamine, 2-hydroxyheptadecylenecylimidazoline

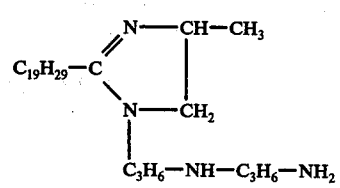

1-aminopropylaminopropyl, 2-abietyl, 4-methylimidazoline

Tetrahydropyrimidines from monocarboxylic acids and trimethylenepolyamines.

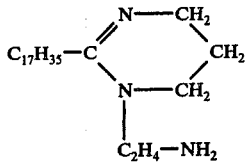

1-aminoethyl, 2-heptadecyltetrahydropyrimidine

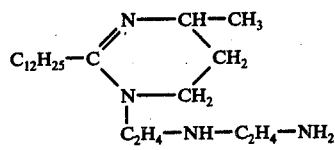

1-aminoethylaminoethyl, 2-dodecyl, 4-methyl tetrahydropyrimidine

Reaction conditions for step (a). The reaction between amines and propane sultone is very facile and occurs quite readily at temperatures from 30° – 70° in a solvent such as methanol. Step (b) takes place at low pH and is most conveniently performed in aqueous HCl. Thus the amino sulfonate and phosphorous acid are heated in hydrochloric acid during the addition of formaldehyde usually at reflux.

The following examples illustrate the procedures:

EXAMPLE 1

Propane sultone (61g, 0.5 mole) was added in 5 mins. to a solution of cyclohexylamine (50g; 0.5 mole) in methanol (200 ml) at room temperature. After completion of the addition the reaction temperature rose to 50° and was maintained at this temperature by slight cooling. A white solid rapidly separated and after a further 4 hr. stirring the reaction mixture was filtered. The white solid was collected, 102g (92%), mp > 300° identified as 3-cyclohexylamino propylsulfonic acid.

Analysis, calculated for $C_9H_{19}NO_3S$, N, 6.34%, S, 14.47% Found N, 6.30%, S, 13.8%

3-cyclohexylamino propylsulfonic acid (50g; 0.23 mole) and phosphorous acid (18.5g; 0.23 mole) were dissolved in a mixture of water (25 ml) and hydrochloric acid (25 ml) and heated to 100° (gentle reflux). To this solution was added 37% aqueous formaldehyde (28g; 0.34 mole) dropwise in 70 min. at 100°–102°. Heating at reflux was continued for a further 3 hr. Evaporation of the aqueous acid gave a quantitative yield of phosphonic sulfonic acid as a viscous gum. This gum was crystallized from ethanol to yield pure product mp 192°–5°.

Analysis, calculated for $C_{10}H_{22}NO_6PS$: N, 4.65%, P, 9.85%, S, 10.15%. Found: N, 4.59%, P, 9.12%, S, 10.6%.

This data, together with NMR spectra confirm the structure as follows:

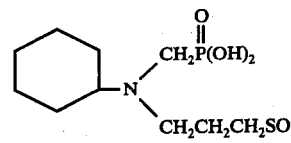

(as a switterion).

EXAMPLE 2

Propanesultone (61g; 0.5 mole) was added to a stirred solution of n-butylamine (36.5g; 0.5 mole) in methanol (200 ml) in 10 min. The reaction temperature was kept at 50°–55° by cooling. After stirring 40 min, a white solid began to separate. After stirring overnight filtration yielded 3-butylaminopropylsulfonic acid 94g (96%).

A solution of this aminosulfonic acid (40g; 0.2 mole) and phosphorous acid (16.8g; 0.2 mole) in 18% HCl (50 ml) was heated at reflux while 37% formaldehyde (25g; 0.3 mole) was added dropwise during 1 hr. The reaction was completed by heating a further 3 hours at reflux to yield the sulfonic/phosphonic acid as a clear viscous gum upon removal of solvent. The product is represented by the structure:

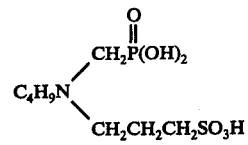

EXAMPLE 3

In the manner of previous Examples n-hexylamino was reacted with propanesultone to yield the 3-hexylamino propylsulfonic acid, mp Analysis, calculated N, 6.27%, S, 14.35%. Found, N, 6.02%, S, 14.55

3-Hexylamino propylsulfonic acid (0.49 mole) was reacted with phosphorous acid (0.49 mole) and formaldehyde (0.50 mole) in presence of hydrochloric acid (100 ml) and water (100 ml). The crystalline product obtained from aqueous ethanol, mp 144°–7°, 79g was the pure phosphonic-sulfonic acid of the following formula:

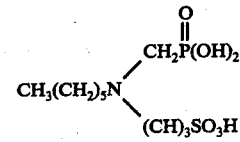

Analysis, Calculated: N, 4.42; P, 9.78; S, 10.10%. Found: N, 4.34; P, 9.79; S, 10.37%

EXAMPLE 4 n-Octylamine was converted into the expected octylaminopropylsulfonic acid by reaction with propanesultone in methanol.

Analysis; Calculated: N, 5.58; S, 12.75% Found: N, 5.35; S, 12.19%

This sulfonic acid (0.2 mole) was reacted with phosphorous acid (0.2 mole) and formaldehyde (0.2 mole) as in previous examples. Crystallization gave the pure sulfonic-phosphonic acid mp 143°–5°, 39.3 g.

Analysis: Calculated: N, 4.06; P, 8.97; S, 9.26%
Found: N, 4.23; P, 8.50; S, 10.2%

In a similar manner the following compounds were prepared:

$$R-N\begin{array}{c}CH_2P(OH)_2\\\parallel\\O\end{array}\\(CH_2)_3SO_3H$$

| | | Analysis | | | | | |
|---|---|---|---|---|---|---|---|
| | | Found | | | Calculated | | |
| Example | R | N | S | P | N | S | P |
| Example 5 | $C_{12}H_{25}$ | 3.31 | 7.81 | 7.92 | 3.49 | 7.98 | 7.73 |
| Example 6 | $C_{16}H_{33}$ | 2.90 | 6.52 | 6.60 | 3.06 | 7.00 | 6.78 |
| Example 7 | $C_{18}H_{37}$ | 2.41 | 6.30 | 6.21 | 2.89 | 6.54 | 6.39 |

The following examples illustrate the reactions of polyamines:

EXAMPLE 8

To a solution of ethylene diamine (30g; 0.5 mole) in methanol (200 ml) was added propane sultone (61g; 0.5 mole) during 15 mins. with slight cooling. After stirring overnight at ambient-temperature the solvent was removed to yield a viscous gum. NMR spectrum was consistent with the expected structure:

$$NH_2-CH_2CH_2NH-CH_2CH_2CH_2SO_3H$$

Analysis: Found, S, 17.57% Calculated S, 17.58%

EXAMPLE 9

In a similar manner to Example 8 ethylene diamine yielded a disulfonic acid, mp 259°–61°.

Analysis: Found, N, 9.11; S, 21.5%. Calculated, N, 9.20; S, 21.0% The product is mainly $$\begin{array}{c}H\\N(CH_2)_3SO_3H\\CH_2\\|\\CH_2\\N(CH_2)_3SO_3H\\H\end{array}$$

EXAMPLE 10

The amino sulfonic acid of Example 8 (0.1 mole) was dissolved in a mixture of hydrochloric acid (20 ml), water (20 ml) and phosphorous acid (8.2g; 0.1 mole). The mixture was heated to 100° and aqueous formaldehyde (0.1 mole) was added during 50 mins. Heating was continued for 4 hrs. at which time aqueous acid was removed in vacuo. The residue was crystallized from aqueous ethanol to yield white crystals mp 156°–8° C. The product is mainly $$(HO)_2\overset{O}{\overset{\parallel}{P}}CH_2\overset{H}{N}-CH_2CH_2\overset{H}{N}CH_2CH_2CH_2SO_3H$$

EXAMPLE 11

The amino propyl sulfonic acid of Example 9 (0.2 mole) was dissolved in a mixture of hydrochloric acid (40 ml), water (40 ml) and phosphorous acid (0.4 mole). Upon heating to 100° 40% aqueous formaldehyde (0.4 mole) was added during 1 hr. The reaction was completed by heating at 100°–102° for 4 hrs. Evaporation of the aqueous acid yielded the product as a gum. The structure is mainly:

$$(HO)_2\overset{O}{\overset{\parallel}{P}}CH_2\diagdown_{N}\diagup^{CH_2-CH_2-N}\diagup^{CH_2\overset{O}{\overset{\parallel}{P}}(OH)_2}_{(CH_2)_3SO_3H}\\HO_3S(CH_2)_3$$

EXAMPLE 12

To a solution of diethylene triamine (0.5 mole) in methanol (200 ml) was added propane sultone (0.5 mole) during 10 mins. Upon completion of the addition the temperature rose to 70°. After the temperature of the solution subsided to 30° the methanol was removed to yield a partially crystalline syrupy mass. NMR spectrum indicated that the product was a mixture with main components.

$$NH_2(CH_2)_2NH(CH_2)_2NH(CH_2)_3SO_3H \quad (A)$$

$$\begin{array}{c}NH_2(CH_2)_2\diagdown\\N(CH_2)_3SO_3H\\H_2N(CH_2)_2\diagup\end{array} \quad (B)$$

(A) was the major component.

EXAMPLE 13

By the procedure of Example 12 diethylene triamine (0.25 mole) was reacted with propane sultone (0.5 mole). The product was a viscous gum whose NMR spectrum indicated the structure to be as follows:

$$HO_3S(CH_2)_3N(CH_2)_2\overset{H}{N}(CH_2)_2NH(CH_2)_3SO_3H$$

Analysis Calculated: N, 12.1%, S, 18.45% Found: N, 11.33%, S, 18.23%

EXAMPLE 14

The amino propyl sulfonic acid of Example 12 (0.5 mole) was dissolved in a mixture of hydrochloric acid (200 ml) water (200 ml) and phosphorous acid (2.0 mole) and heated at 100° C. To this solution was added 40% aqueous formaldehyde (2.1 mole) during 75 mins. The reaction was completed by heating at gentle reflux for 3 hr. The product is substantially:

$$\left[(HO)_2\overset{O}{\overset{\parallel}{P}}CH_2\right]_2N(CH_2)_2-N(CH_2)_2N(CH_2)_3SO_3H\\\qquad\qquad\qquad|\\\qquad\qquad\qquad CH_2P(OH)_2CH_2P(OH)_2\\\qquad\qquad\qquad\qquad\overset{\parallel}{O}$$

with some product from isomer B.

EXAMPLE 15

The aminopropylsulfonic acid of Example 13 (.24 mole) was dissolved in a mixture of hydrochloric acid (150 ml), water (150 ml) and phosphorous acid (0.72 mole) and heated to 100° C. At this temperature 40% aqueous formaldehyde (0.75 mole) was added in 1 hr. and the reaction completed by heating for 3 hours. Evaporation of the aqueous acid yielded the sulfonic/phosphonic acid. The main component is:

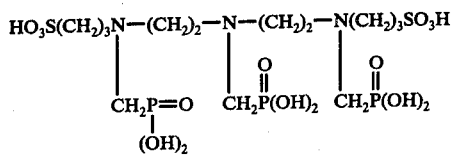

USE AS SCALE INHIBITOR

Most commercial water contains alkaline earth metal cations, such as calcium, barium, magnesium, etc., and anions such as bicarbonate, carbonate, sulfate, oxalate, phosphate, silicate, fluoride, etc. When combinations of these anions and cations are present in concentrations which exceed the solubility of their reaction products, precipitates form until their product solubility concentrations are no longer exceeded. For example, when the concentrations of calcium ion and carbonate ion exceed the solubility of the calcium carbonate reaction product, a solid phase of calcium carbonate will form as a precipitate.

Solubility product concentrations are exceeded for various reasons, such as evaporation of the water phase, change in pH, pressure or temperature, and the introduction of additional ions which can form insoluble compounds with the ions already present in the solution.

As these reaction products precipitate on the surfaces of the water-carrying system, they form scale. The scale prevents effective heat transfer, interferes with fluid flow, facilitates corrosive processes, and harbors bacteria. Scale is an expensive problem in many industrial water systems, causing delays and shutdowns for cleaning and removal.

Scale-forming compounds can be prevented from precipitating by inactivating their cations with chelating of sequestering agents, so that the solubility of their reaction products is not exceeded. Generally, this approach requires many times as much chelating or sequestering agent as cation present, and the use of large amounts of treating agent is seldom desirable or economical.

More than twenty-five years ago it was discovered that certain inorganic polyphosphates would prevent such precipitation when added in amounts far less than the concentrations needed for sequestering or chelating. See, for example, Hatch and Rice, "Industrial Engineering Chemistry," vol. 31, p. 51, at 53; Reitemeier and Buchrer, "Journal of Physical Chemistry," vol. 44, No. 5, p. 535 at 536 (May 1940); Fink and Richardson U.S. Pat. No. 2,358,222; and Hatch U.S. Pat. No. 2,539,305. When a precipitation inhibitor is present in a potentially scale-forming system at a markedly lower concentration than that required for sequestering the scale forming cation, it is said to be present in "threshold" amounts. Generally, sequestering takes place at a weight ratio of threshold active compound to scale-forming cation component of greater than about ten to one, and threshold inhibition generally takes place at a weight ratio of threshold active compound to scale-forming cation component of less than about 0.5 to 1.

The "threshold" concentration range can be demonstrated in the following manner. When a typical scale-forming solution containing the cation of a relatively insoluble compound is added to a solution containing the anion of the relatively insoluble compound and a very small amount of a threshold active inhibitor, the relatively insoluble compound will not precipitate even when its normal equilibrium concentration has been exceeded. If more of the threshold active compound is added, a concentration is reached where turbidity or a precipitate of uncertain composition results. As still more of the threshold active compound is added, the solution again becomes clear. This is due to the fact that threshold active compounds in high concentrations also act as sequestering agents, although sequestering agents are not necessarily "threshold" compounds. Thus, there is an intermediate zone between the high concentrations at which they act as threshold inhibitors. Therefore, one could also define "threshold" concentrations as all concentrations of threshold active compounds below that concentration at which this turbid zone or precipitate is formed. Generally the threshold active compound will be used in a weight ratio of the compound to the cation component of the scale-forming salts which does not exceed about 1.

The polyphosphates are generally effective threshold inhibitors for many scale-forming compounds at temperatures below 100° F. But after prolonged periods at higher temperatures, they lose some of their effectiveness. Moreover, in an acid solution, they revert to ineffective or less effective compounds.

A compound that has sequestering powers does not predictably have threshold inhibiting properties. For example, ethylenediamine tetracetic acid salts are powerful sequesterants but have no threshold activities.

We have now discovered a process for inhibiting scale such as calcium, barium and magnesium carbonate, sulfate, silicate, etc., scale which comprises employing threshold amounts of the compositions of this invention.

In general it is preferred that at least 50% but preferably at least 80% of the nitrogen-bonded hydrogens of the polyamine be replaced by sulfonate or phosphonate groups.

Scale formation from aqueous solutions containing an oxide variety of scale forming compounds, such as calcium, barium and magnesium carbonate, sulfate, silicate, oxalates, phosphates, hydroxides, fluorides and the like are inhibited by the use of threshold amounts of the compositions of this invention which are effective in small amounts, such as less than 100 ppm and are preferably used in concentrations of less than 25 ppm.

The compounds of the present invention (e.g., the acid form of the compounds) may be readily converted into the corresponding alkali metal, ammonium or alkaline earth metal salts by replacing at least half of the hydrogen ions in the phosphonic acid group with the appropriate ions, such as the potassium ion or ammonium or with alkaline earth metal ions which may be converted into the corresponding sodium salt by the addition of sodium hydroxide. If the pH of the amine compound is adjusted to 7.0 by the addition of caustic soda, about one half of the —OH radicals on the phosphorous atoms will be converted into the sodium salt form.

The scale inhibitors of the present invention illustrate improved inhibiting effect at high temperatures when compared to prior art compounds. The compounds of the present invention will inhibit the deposition of scale-forming alkaline earth metal compounds on a surface in contact with aqueous solution of the alkaline earth metal compounds over a wide temperature range. Generally, the temperatures of the aqueous solution will be at least 40° F., although significantly lower temperatures will often be encountered. The preferred temperature range for inhibition of scale deposition is from about 130° to about 350° F. The aqueous solutions of brines requiring treatment generally contain about 50 ppm to about 50,000 ppm of scale-forming salts. The compounds of the present invention effectively inhibit scale formation when present in an amount of from 0.1 to about 100 ppm, and preferably 0.2 to 25 ppm wherein the amounts of the inhibitor are based upon the total aqueous system. There does not appear to be a concentration below which the compounds of the present invention are totally ineffective. A very small amount of the scale inhibitor is effective to a correspondingly limited degree, and the threshold effect is obtained with less than 0.1 ppm. There is no reason to belive that this is the minimum effective concentration. The scale inhibitors of the present invention are effective in both brine, such as sea water, and acid solutions.

Calcium Scale Inhibition Test

The procedure utilized to determine the effectiveness of scale inhibitors in regard to calcium scale is as follows:

Several 50 ml. samples of a 0.04 sodium bicarbonate solution are placed in 100 ml. bottles. To these solutions is added the inhibitor in various known concentrations. 50 ml. samples of a 0.02 M $CaCl_2$ solution are then added.

A total hardness determination is then made on the 50–50 mixture utilizing the well known Schwarzenbach titration. The samples are placed in a water bath and heated at 180° F. 10 ml. samples are taken from each bottle at 2 and 4 hour periods. These samples are filtered through millipore filters and the total hardness of the filtrates are determined by titration.

$$\frac{\text{Total hardness after heating}}{\text{Total hardness before heating}} \times 100 = \% \text{ inhibition}$$

Calcium Scale Inhibition.

| Compound | Concentration | % Inhibition |
|---|---|---|
| Example 1 | 100 ppm | 86% |
| Example 4 | 100 ppm | 24% |
| Example 4 | 200 ppm | 60% |
| Example 11 | 50 ppm | 95% |
| Example 11 | 100 ppm | 100% |
| Example 14 | 10 ppm | 66% |
| Example 14 | 100 ppm | 100% |
| Example 15 | 10 ppm | 42% |
| Example 15 | 50 ppm | 95% |

We claim:

1. A compound which is an amine containing the following nitrogen-bonded groups:

$$-(CH_2)_3SO_3M$$

$$-\underset{R'}{\overset{R}{\underset{|}{C}}}-P(OM)_2 \quad \overset{O}{\underset{\|}{}}$$

where R and R' are hydrogen or an alkyl or aryl group and M is hydrogen or a salt moiety, the nitrogen to which the groups are bonded being amino nitrogen of the amine, the salt moiety being an alkali metal, an alkaline earth metal, ammonium or ammonium form of an amine, the compound in acid form having the $$-(CH_2)_3SO_3H \quad \text{and} \quad -\underset{R'}{\overset{R}{\underset{|}{C}}}-\overset{O}{\underset{\|}{P}}(OH)_2$$

as the sole acidic groups, the compound with hydrogen in place of said groups being an amine in which said nitrogen is amino nitrogen.

2. The compound of claim 1 where the $-(CH_2)_3SO_3M$ and $$-\underset{R'}{\overset{R}{\underset{|}{C}}}-\overset{O}{\underset{\|}{P}}(OM)_2$$

groups are bonded to the same nitrogen atom, where M is hydrogen, alkali metal, alkaline earth metal or ammonium.

3. The compound of claim 2 of the formula $$R-N\overset{\diagup (CH_2)_3SO_3M}{\diagdown \underset{CH_2P(OM)_2}{\overset{O}{\underset{\|}{}}}}$$

where R is a hydrocarbon group.

4. The compound of claim 1 where the compound has at least 2 nitrogen atoms, all of the valences of the nitrogen atoms of the compound being attached to carbon or hydrogen, and where M is hydrogen, alkali metal, alkaline earth metal or ammonium.

5. The compound of claim 4 where the compound has the formula $$-\underset{|}{\overset{|}{N}}(AN)_{\overline{n}}$$

where $n=1-4$,
where the nitrogen valences are joined to hydrogen, $(CH_2)_3SO_3M$ or $$-CH_2\overset{O}{\underset{\|}{P}}(OM)_2$$

with the proviso that that compound contain at least one $-(CH_2)_3SO_3M$ and at least one $$-CH_2\overset{O}{\underset{\|}{P}}(OM)_2,$$

and where A is alkylene.

6. The compound of claim 5 where in at least one instance the $-(CH_2)_3SO_3M$ and $$-CH_2\overset{O}{\underset{\|}{P}}(OM)_2$$

groups are bonded to the same nitrogen.

7. The compound of claim 5 where the compound contains no nitrogen-bonded hydrogens.

8. The compound of claim 6 which is derived from ethylene diamine or ethylene triamine.
9. The compound of claim 8 having the formula
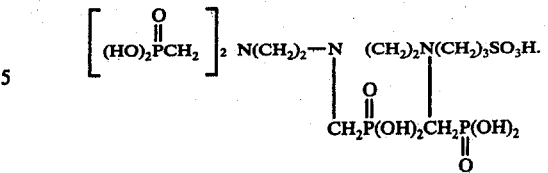
10. The compound of claim 8 having the formula
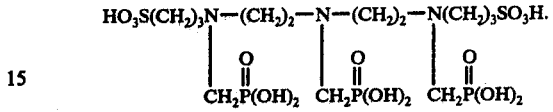
* * * * *

UNITED STATES PATENT AND TRADEMARK OFFICE
CERTIFICATE OF CORRECTION

PATENT NO. : 4,085,134
DATED : April 18, 1978
INVENTOR(S) : Derek Redmore and Frederick T. Welge It is certified that error appears in the above-identified patent and that said Letters Patent are hereby corrected as shown below:

Column 15, second line of claim 8,
"ethylene diamine or ethylene triamine" should read
--- ethylene diamine or diethylene triamine ---

Signed and Sealed this

*Seventh* Day of *November 1978*

[SEAL]

Attest:

RUTH C. MASON
*Attesting Officer*

DONALD W. BANNER
*Commissioner of Patents and Trademarks*